US 8,110,697 B2

(12) United States Patent
Jandke et al.

(10) Patent No.: US 8,110,697 B2
(45) Date of Patent: Feb. 7, 2012

(54) METHOD FOR THE PRODUCTION OF POLYMERIZABLE SILICONES

(75) Inventors: Markus Jandke, Burgkirchen (DE); Florian Koopmann, Burghausen (DE); Birgit Peschanel, Burghausen (DE)

(73) Assignee: Wacker Chemie AG, Munich (DE)

( * ) Notice: Subject to any disclaimer, the term of this patent is extended or adjusted under 35 U.S.C. 154(b) by 355 days.

(21) Appl. No.: 12/520,248

(22) PCT Filed: Jan. 8, 2008

(86) PCT No.: PCT/EP2008/050110
§ 371 (c)(1),
(2), (4) Date: Jun. 19, 2009

(87) PCT Pub. No.: WO2008/090013
PCT Pub. Date: Jul. 31, 2008

(65) Prior Publication Data
US 2010/0029972 A1    Feb. 4, 2010

(30) Foreign Application Priority Data

Jan. 24, 2007  (DE) .......................... 10 2007 003 579

(51) Int. Cl.
*C07F 7/18* (2006.01)

(52) U.S. Cl. ........ 556/462; 556/445; 556/446; 556/450; 556/451; 556/453

(58) Field of Classification Search .................. 556/462, 556/445, 446, 450, 451, 453
See application file for complete search history.

(56) References Cited

FOREIGN PATENT DOCUMENTS

| EP | 15105201 A | 3/2005 |
|---|---|---|
| EP | 1472264 B | 6/2005 |
| JP | 11217389 A | 8/1999 |
| JP | 2000186095 A | 7/2000 |
| WO | 03064436 A | 8/2003 |

*Primary Examiner* — Elvis O Price
(74) *Attorney, Agent, or Firm* — Brooks Kushman P.C.

(57) ABSTRACT

Polymerizable siloxy-substituted silanes are obtained in high yield and purity by adding a substituted alkoxysilane to a mixture of disiloxane, acetic acid, sulfuric acid, and optionally an acidic catalyst, separating a product phase from an acidic phase, adding hexamethyldisilazane to the product phase and filtering off a resulting salt, followed by distillation.

16 Claims, No Drawings

METHOD FOR THE PRODUCTION OF POLYMERIZABLE SILICONES

CROSS-REFERENCE TO RELATED APPLICATION

This application is the U.S. national phase of PCT Appln. No. PCT/EP2008/050110 filed Jan. 8, 2008 which claims priority to German application DE 10 2007 003 579.0 filed Jan. 24, 2007.

BACKGROUND OF THE INVENTION

1. Field of the Invention

The invention relates to the production of polymerizable silicones comprising siloxy-substituted silane structures. In particular, the invention relates to the production of silanes of high purity having polymerizable groups and substituted with triorganosiloxy groups by substitution of alkoxysilanes with disiloxanes.

2. Description of the Related Art

Polymerizable silicones, such as 3-acryloxypropyltris(trimethylsiloxy)silane, 3-methacryloxypropyltris(trimethylsiloxy)silane, 3-methacryloxypropyltris(dimethylphenylsiloxy)silane, 1-methacryloxymethyltris(trimethylsiloxy)silane, etc. are useful as raw material or monomer for the production of electronic materials, for the production of contact lenses, as raw material in compositions for functional and industrial coatings, polymeric microstructures or cosmetic applications.

The use of polymerizable silicones as raw materials or monomers for the production of electronic materials, for the production of contact lenses and optical components, as raw materials in compositions for functional and industrial coatings, for polymeric microstructures or cosmetic applications, requires the provision of high-purity materials with a reduced content of by-products such as monohydroxysilanes, monoorganoxysilanes and difunctional disiloxanes and also inorganic and metallic impurities.

JP 11-217389 describes a method in which an alkoxy- or aryloxy-substituted silicone (e.g. 3-methacryloxy-propyltrimethoxysilane) is reacted with hexamethyl-disiloxane in the presence of a carboxylic acid (e.g. acetic acid) and an acidic catalyst (trifluoro-methanesulfonic acid), giving a siloxy-substituted product. The method is preferably designed so that hexamethyldisiloxane, carboxylic acid and catalyst are initially introduced before the alkoxy or aryloxy component is added and the reaction is carried out at ca. 20-70° C. By adding a small amount of hexamethyldisilazane (0.0025 mol per mole of alkoxysilane), the reaction is stopped and neutralized, giving a product with reduced purity (<90 area %). The ratio of product G-Si(OSiMe$_3$)$_3$ [G=methacryloxypropyl] to the monoorganoxy by-product G-Si(OMe)(OSiMe$_3$)$_2$ is ca. 8.3 (i.e. ca. 10.7% monoorganoxy by-product). The ratio of product to the difunctional by-product G-[Me$_3$SiO]$_2$Si—O—Si[OSiMe$_3$]$_2$-G is 54.9 (i.e. ca. 1.8% difunctional disiloxane). It is described how through appropriate temperature control the condensation of silanol groups present to difunctional disiloxane is suppressed, but not how the content of monohydroxysilane (silanol) can be limited. The high content of impurities is problematic as regards the aforementioned applications.

From JP 2000-186095 it is known to react hexamethyldisiloxane, a carboxylic acid (acetic acid) and a strong acid (concentrated sulfuric acid) with 3-methacryloxypropyltrimethoxysilane, the latter preferably being added at a temperature of from −10° C. to 0° C. over the course of 30 min. Following the post reaction, washing and distillation, 3-methacryloxy-propyltris(trimethylsiloxysilane) is obtained with a purity of 90.2-97.8%. The product is contaminated with monohydroxy by-product and dimer by-product (difunctional disiloxane). Besides the high content of the specified impurities (in particular difunctional disiloxane), a considerable disadvantage of the method is that following the actual reaction, a lengthy and therefore uneconomical aging of the reaction mixture at various temperatures over a period of 24 h has to be accepted. The aging process is an essential part of the method since during the reaction monohydroxy by-products are formed whose content is reduced in the course of the aging process by converting the silanols into difunctional disiloxane via a dehydrogenation. In this connection, contents of difunctional disiloxane up to 10% are obtained, which is unacceptable for a number of applications.

EP 1510520 A describes the production of high-purity branched siloxanes with a reduced content of monoorganoxysilane or monohydroxysilane impurities in a two-stage process via the post-reaction of a contaminated crude product (following complete or following partial work-up and/or isolation) with disiloxane and acid in high yield. However, the cited method has the disadvantage that, firstly, on account of the aqueous work-up, monohydroxysilane and/or monoorganox impurities can still continue to form in the acidic medium. The after-treatment can reduce the content of monoorganoxysilane or monohydroxysilane contamination. Secondly, the essential disadvantage of the method is that prior to the post-reaction, the crude product must be worked up completely or at least partially and that consequently the washings, phase separations (and optionally also distillations) are to be carried out twice.

EP 1472264 A describes a method for the production of high-purity silicone compounds via the substitution of alkoxy, aryloxy or acyloxy groups by trialkylsiloxy units. In the presence of a carboxylic acid (acetic acid), an acidic catalyst (CF$_3$SO$_3$H), a disiloxane (Me$_3$SiOSiMe$_3$), the reaction is started by adding an alkoxy- or aryloxysilane.

A carboxylic anhydride (e.g. acetic anhydride) is then added. The reaction system remains largely single-phase, which increases the amount of the base to the used for the neutralization.

For example, 3-methacryloxypropyltris(trimethylsiloxysilane) is obtained in high yield with a purity of 98.7%, the impurities obtained being 1.3% disiloxane (dimer) and less than 0.5% of the monoorganoxysilane by-product CH$_2$=CH(CH$_3$)COO—(CH$_2$)$_3$—Si(OMe)(OSiMe$_3$)$_3$. For further products, considerably lower purities (down to 93%) and higher contents of dimeric compounds (up to 4.4%) are measured. However, how the content of monohydroxysilane by-product can be kept low until isolation of the product and how its formation can be prevented in the course of the work-up/neutralization is not described.

Besides the high required amount of carboxylic anhydride, the essential disadvantage of the cited method is that the content of difunctional impurities (disiloxane) is furthermore above 1% and upon dispensing with a distillation, also inorganic and polymeric organic impurities are said to be present. In the case of a distillation, a significantly lower yield would be expected. Especially for the production of electronic and optical media and components, for the production of contact lenses and also for use in functional coatings, a markedly lower content of difunctional impurities is required. In these applications, in particular the content of difunctional silicones in the polymerizable silicone is troublesome since it triggers, by increasing the crosslinking density, a modification of the mechanical and thus also of the optical properties and/or of the desired properties for use in the sector of electronic materials or functional coatings. Residual contents of monohydroxy and monomethoxy impurities can lead in these applications, as a result of cleavage reaction and/or condensation reactions, to an subsequent change in the functional properties of the materials, components or coatings. Residual contents of inorganic salts or polymeric fractions can lead to undesired light scattering and inadequate performance of optical components. In electronic materials, in this case a significant change in the insulation effect/conductivity and the breakdown field strength is to be expected. Surface properties of functional coatings can be lastingly adversely affected by said impurities. It is therefore essential that polymerizable silicones are made available in high-purity form with a minimum content of difunctional silicones, still condensation-reactive silicones and also inorganic impurities.

SUMMARY OF THE INVENTION

It was an object of the invention to provide a method for the production of polymerizable silicones of high purity in which the disadvantages described above are avoided, and in which polymerizable silicones of high purity with a content of at least 98.5% are obtained which have, as by-products, a content of less than 0.4% of difunctional disiloxane and of less than 0.4% each of monohydroxy and/or monoalkoxy structures. These and other objects are achieved by the invention, wherein disiloxanes are introduced into the reaction with acetic acid, sulfuric acid, and optionally acidic catalyst(s), alkoxysilane is metered in at low temperature, an organic phase is separated from an organic phase, and hexamethyldisilazane is, added to the organic phase, which is then worked up by distillation and optional filtering.

DETAILED DESCRIPTION OF THE PREFERRED EMBODIMENTS

The invention thus provides a method for the production of high-purity polymerizable silicones of the formula

  (I)

by
(a) initially introducing disiloxane (1) of the formula $(R^1)_3SiOSi(R^1)_3$  (II)

in the presence of acetic acid (2), sulfuric acid (3), preferably concentrated sulfuric acid, and optionally acidic catalyst (4),
(b) at a temperature of from −20° to 0° C., metering in a substituted alkoxysilane (5) of the formula

,  (III)

(c) following phase separation, separating off an acid phase (lower layer),
(d) adding 0.02-1.0 mol of hexamethyldisilazane (6), based on 1 mol of alkoxysilane (5),
(e) after filtering off the resulting salt,
  removing the readily volatile constituents and distilling the product, and optionally
(f) then filtering the product,
where
$R^1$ is identical or different and is a hydrogen atom or an optionally substituted monovalent hydrocarbon radical having 1 to 18 carbon atoms,
$R^2$ is identical or different and is a hydrogen atom or an optionally substituted monovalent hydrocarbon radical having 1 to 18 carbon atoms, $R^3$ is identical or different and is an alkyl radical having 1 to 18 carbon atoms which is optionally substituted with alkoxy groups,
Sp is a single bond or a divalent hydrocarbon radical having 1 to 8 carbon atoms,
Y is a single bond or —O—,
P is an acryloxy, methacryloxy, vinyl or allyl radical,
n is 0, 1 or 2, preferably 0.

The invention further provides high-purity polymerizable silicones of the formula

  (I)

which have a purity of at least 98.5%, preferably at least 99.0%,
a content of less than 0.4%, preferably less than 0.2%, of difunctional disiloxane of the formula $[P-Y-Sp-Si(R^2)_n(OSiR^1_3)_{(2-n)}]_2O$, of less than 0.4%, preferably less than 0.3%, of monohydroxysilane of the formula

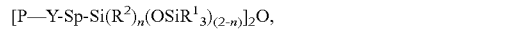

and less than 0.4%, preferably less than 0.3%, of monoalkoxysilane of the formula

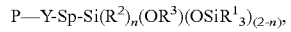, where $R^1$, $R^2$, $R^3$, Sp, Y, P and n have the meaning given above.

Examples of $R^1$ are alkyl, alkenyl, alkynyl and aryl radicals having 1-18 carbon atoms, preferably 1-15 carbon atoms, more preferably 1-9 carbon atoms. Examples of $R^1$ are alkyl radicals such as the methyl, ethyl, n-propyl, isopropyl, n-butyl, isobutyl, tert-butyl, n-pentyl, n-hexyl and n-octyl radicals; cycloalkyl radicals such as the cyclopentyl and cyclohexyl radicals; alkenyl and alkynyl radicals such as the vinyl, propenyl, allyl and ethinyl radicals; and aryl radicals such as the phenyl radical.

Examples of $R^2$ are alkyl, alkenyl, alkynyl and aryl radicals having 1-18 carbon atoms, preferably 1-9 carbon atoms, more preferably 1-6 carbon atoms. Examples of $R^2$ are alkyl radicals such as the methyl, ethyl, n-propyl, isopropyl, n-butyl, isobutyl, tert-butyl, n-pentyl, n-hexyl and n-octyl radicals; cycloalkyl radicals such as the cyclopentyl and cyclohexyl radicals; alkenyl and alkynyl radicals such as the vinyl, propenyl, allyl and ethinyl radicals; and aryl radicals such as the phenyl radical.

Examples of $R^3$ are alkyl radicals having 1 to 3 carbon atoms optionally substituted with alkoxy groups. Examples of $R^3$ are the methyl, ethyl, and propyl radicals.

Examples of Sp are alkylene or cycloalkylene radicals, such as —CH$_2$—, —CH$_2$—CH$_2$— and —CH$_2$—CH$_2$—CH$_2$— radicals, C$_4$-C$_8$-alkylene radicals and cyclohexylene radicals.

Y is preferably —O—.
P is preferably an acryloxy and methacryloxy radical.
Examples of disiloxanes of the formula $(R^1)_3SiOSi(R^1)_3$ are
hexamethyldisiloxane,
hexaethyldisiloxane,
1,3-di-tert-butyl-1,1,3,3-tetramethyldisiloxane,
1,1,3,3-tetramethyldisiloxane,
1,3-divinyl-1,1,3,3-tetramethyldisiloxane and
1,3-diphenyl-1,1,3,3-tetramethyldisiloxane.
Examples of alkoxysilanes are:
1-acryloxymethyltrimethoxysilane,
2-acryloxyethyltrimethoxysilane,
3-acryloxypropyltrimethoxysilane, 1-methacryloxymethyltrimethoxysilane,
1-methacryloxymethyldimethoxymethylsilane,
2-methacryloxyethyltrimethoxysilane,
3-methacryloxypropyltrimethoxysilane,
1-acryloxymethyltriethoxysilane,
2-acryloxyethyltriethoxysilane,
3-acryloxypropyltriethoxysilane,
1-methacryloxymethyltriethoxysilane,
2-methacryloxyethyltriethoxysilane,
3-methacryloxypropyltriethoxysilane,
4-methacryloxybutyltrimethoxysilane,
6-methacryloxyhexyltrimethoxysilane,
8-methacryloxyoctyltrimethoxysilane,
methacryloxycyclohexyltrimethoxysilane, and
vinyltrimethoxysilane.

The alkoxysilanes used are already substituted with one polymerizable group. In order to avoid a polymerization of the polymerizable group, it is also possible to use alkoxysilanes which are already provided with a low content of a stabilizer. Alternatively, a stabilizer can be added to the reaction mixture (0-5000 ppm, preferably 0-3000 ppm, based on alkoxysilane used).

Particularly preferred alkoxysilanes are:
3-methacryloxypropyltrimethoxysilane,
1-methacryloxymethyltrimethousilane,
1-methacryloxymethyldimethoxymethylsilane, and vinyltrimethoxysilane.

Examples of polymerizable silicones of the formula P—Y-Sp-Si($R^2$)$_n$(OSi$R^1_3$)$_{(3-n)}$ are
1-acryloxymethyltris(trimethylsiloxy)silane,
2-acryloxyethyltris(trimethylsiloxy)silane,
3-acryloxypropyltris(trimethylsiloxy)silane,
1-methacryloxymethyltris(trimethylsiloxy)silane,
2-methacryloxyethyltris(trimethylsiloxy)silane,
3-methacryloxypropyltris(trimethylsiloxy)silane,
4-methacryloxybutyltris(trimethylsiloxy)silane,
6-methacryloxyhexyltris(trimethylsiloxy)silane,
8-methacryloxyoctyltris(trimethylsiloxy)silane,
methacryloxycyclohexyltris(trimethylsiloxy)silane,
1-acryloxymethylbis(trimethylsiloxy)methylsilane,
2-acryloxyethylbis(trimethylsiloxy)methylsilane,
3-acryloxypropylbis(trimethylsiloxy)methylsilane,
1-methacryloxymethylbis(trimethylsiloxy)methylsilane,
2-methacryloxyethylbis(trimethylsiloxy)methylsilane,
3-methacryloxypropylbis(trimethylsiloxy)methylsilane,
1-methacryloxymethyltris(dimethylvinylsiloxy)silane,
3-methacryloxypropyltris(dimethylvinylsiloxy)silane,
and
vinyltris(trimethylsiloxy)silane.

Preferred examples of polymerizable compounds P—Y-Sp-Si($R^2$)$_n$(OSi$R^1_3$)$_{(3-n)}$ are
3-acryloxypropyltris(trimethylsiloxy)silane,
3-methacryloxypropyltris(trimethylsiloxy)silane,
3-methacryloxypropyltris(dimethylphenylsiloxy)silane,
1-methacryloxymethyltris(trimethylsiloxy)silane,
1-methacryloxymethylbis(trimethylsiloxy)methylsilane,
and
vinyltris(trimethylsiloxy)silane.

Examples of monohydroxysilane impurities P—Y-Sp-Si($R^2$)$_n$(OH)(OSi$R^1_3$)$_{(2-n)}$ are
3-acryloxypropylbis(trimethylsiloxy)silanol,
3-methacryloxypropylbis(trimethylsiloxy)silanol,
3-methacryloxypropylbis(dimethylphenylsiloxy)silanol,
1-methacryloxymethylbis(trimethylsiloxy)silanol,
1-methacryloxymethyl(trimethylsiloxy)methylsilanol, and
vinylbis(trimethylsiloxy)silanol.

Examples of monoorganoxysilane impurities P—Y-Sp-Si($R^2$)$_n$(O$R^3$)(OSi$R^1_3$)$_{(2-n)}$ are
3-acryloxypropylbis(trimethylsiloxy)methoxysilane,
3-methacryloxypropylbis(trimethylsiloxy)methoxysilane,
3-methacryloxypropylbis(dimethylphenylsiloxy)methoxysilane,
1-methacryloxymethylbis(trimethylsiloxy)methoxysilane,
1-methacryloxymethyl(trimethylsiloxy)methoxymethylsilane
and
vinylbis(trimethylsiloxy)methoxysilane.

Examples of impurities with difunctional disiloxanes of the formula [P—Y-Sp-Si($R^2$)$_n$(OSi$R^1_3$)$_{(2-n)}$]$_2$O are
1,3-bis(3-acryloxypropyl)-1,1,3,3-tetra(trimethylsiloxy)disiloxane,
1,3-bis(3-methacryloxypropyl)-1,1,3,3-tetra(trimethylsiloxy)disiloxane,
1,3-bis(1-methacryloxymethyl)-1,1,3,3-tetra(trimethylsiloxy)disiloxane,
1,3-bis(1-methacryloxypropyl)-1,1,3,3-tetra(dimethylphenylsiloxy)disiloxane,
1,3-bis(3-methacryloxypropyl)-1,3-bis(trimethylsiloxy)-1,3-dimethyldisiloxane and
1,3-divinyl-1,1,3,3-tetra(trimethylsiloxy)disiloxane.

The method according to the invention is described in more detail below:

(a) In a first step, disiloxanes (1) of the formula ($R^1$)$_3$SiOSi($R^1$)$_3$ are initially introduced in the presence of acetic acid (2), sulfuric acid (3), preferably concentrated sulfuric acid, and optionally acidic catalyst (4). The quantitative molar ratio of disiloxane (1) and alkoxysilane (5) here is preferably 0.5 to 1.0 mol, more preferably 0.6 to 0.8 mol, of disiloxane (1) per mole of alkoxy group of the alkoxysilane (5).

The quantitative molar ratio between acetic acid (2) and alkoxysilane (5) here is preferably 1.5 to 6 mol, more preferably 2 to 4 mol of acetic acid (2) per mole of alkoxysilane (4).

The quantitative molar ratio of sulfuric acid (3) and alkoxysilane (5) is preferably 0.1 to 2 mol, more preferably 0.2 to 0.75 mol of sulfuric acid (3) per mole of alkoxysilane (5).

Acidic catalysts which can be used are, for example, concentrated hydrochloric acid, trifluoroacetic acid or trifluoromethanesulfonic acid, but also Lewis acids such as $AlCl_3$ or $TiCl_4$, provided they do not undergo any secondary reaction with further substituents of the alkoxysilane. If acidic catalysts are co-used, 0.001 to 0.01 mol of acidic catalyst (4), based on the amount of alkoxysilane, are used.

(b) The reaction mixture is cooled to a temperature of −20° C. to 0° C., preferably −10° C. to 0° C., in order to minimize condensation reactions with formation of difunctional dimers.

In process step (b), at −20° C. to 0° C., preferably −10 to 0° C., a substituted alkoxysilane of the formula P—Y-Sp-Si($R^2$)$_n$(O$R^3$)$_{(3-n)}$ is metered in.

The alkoxysilane (5) is preferably metered in over the course of 1 h-3 h, more preferably 1 h-2 h, and is then post-reacted for preferably 1 h to 4 h, more preferably 1 h-2 h, at preferably 10-45° C., more preferably at room temperature.

The content of difunctional disiloxane and of monoorganoxysilane is limited by this method even prior to the work-up.

By means of the sulfuric acid (3), water which is formed and methanol are removed from the reaction equilibrium and/or the reaction of the methanol to give methyl acetate is favored, meaning that the contents of monoorganoxy impurities are minimized. The amount of added sulfuric acid should not be exceeded since in this case the formation of dimeric condensation products (difunctional disiloxane) is promoted. If the amount of sulfuric acid is too low, then the minimization of the contents of monoorganoxy impurities is not sufficient. The temperature during the addition of the alkoxysilane plays a further role. At elevated temperature, in the presence of sulfuric acid, difunctional disiloxane (dimer) is formed to an increased degree, which can possibly no longer be sufficiently separated off in the subsequent distillation.

(c) An essential advantage of the method then additionally consists in the fact that after the reaction has taken place, the reaction mixture phase-separates. An acidic phase comprising alcohol, such as MeOH, water, acetic acid, acidic catalyst, can be separated off. This offers firstly the advantage that alcohol, such as MeOH and water are separated off for possible subsequent secondary reactions and secondly that the amount of hexamethyldisilazane to be used for the neutralization is minimized.

(d) Following the reaction of the disiloxane with the alkoxysilane in the presence of acetic acid, sulfuric acid (and optionally acidic catalyst such as trifluoro-methanesulfonic acid), a crude product with a minimum content of by-products is firstly obtained. In order to prevent by-products forming again in the course of the work-up, after the lower phase has been separated off, the reaction mixture is reacted with hexamethyldisilazane and/or non-aqueously neutralized. A further essential advantage of the use of hexamethyldisilazane is that contents of monohydroxysilanes that are still present are reliably eliminated by this treatment. A content of monohydroxysilane which is potentially still present from the reaction in the presence of sulfuric acid is reliably eliminated by this treatment.

In order to minimize the still remaining by-product content of monohydroxysilane, 0.02-1.0 mol, preferably 0.1-0.8 mol, preferably 0.1-0.6 mol of hexamethyl-disilazane (6), are added per mole of alkoxysilane (5) and then after-stirred. The metering and post-reaction preferably takes place within a total time of 1 h-5 h, at preferably 10° C.-40° C.

A neutralization of the reaction mixture prior to the distillation is essential in order to avoid, during the subsequent distillation, the new formation of by-products, in particular difunctional disiloxane, due to a shift in the equilibrium under acidic conditions. Moreover, as a result of dispensing with the use of aqueous neutralizing agents when using hexamethyldisilazane, a subsequent formation of monohydroxy- (and monoorganoxysilanes) as by-product is avoided.

(e) The resulting salts are filtered off, for example, via a pressure suction filter or centrifuge and downstream fine filtration, in which case preferably a sieve/filter with a mesh width of 0.2-2 μm, preferably 0.2-0.5 μm, is used. In order to stabilize the product during and/or after distillation, the addition of stabilizers in the method before or after the distillation step is possible.

The volatile constituents are separated off and then the product is distilled in vacuo. For the distillation, besides conventional distillation methods with or without distillation column, it is also possible to use thermally gentle methods such as thin-film evaporation, short-path evaporation and the like. Furthermore, in the course of the distillation, an additional separating off of inorganic impurities, e.g. salts, takes place. Besides a high purity, the exclusion of polymeric fractions is also essential both for the processing properties and also the material properties of the polymerizable silicone. In order to avoid the formation of polymer in polymerizable silicones during their synthesis, stabilizers can be added during the reaction or the work-up. On account of the inhibiting effect of oxygen with regard to a potential free-radical polymerization of acrylic groups, methacrylic groups, ethynyl groups or vinyl groups it is also possible to carry out individual process steps under an oxygen partial pressure (e.g. lean air). Additionally, the existence of polymeric impurities in the product is avoided by distilling the product. To stabilize the polymerizable silicone, stabilizers can be added for the storage also after its isolation. The content of added stabilizer here should preferably be between 100 and 5000 ppm (with reference to alkoxysilane (4)), more preferably between 200 and 2000 ppm. Examples of stabilizers are 2,6-di-tert-butyl-4-methylphenol (BHT), 2,6-di-tert-butyl-4-(dimethylaminomethyl)phenol and phenothiazine.

(f) In order to separate off any salts, metals, particles that are still present, the distilled polymerizable silicone is, if appropriate, filtered again. For this, for example, a filter candle with a pore size of 0.1-1 μm, preferably 0.2-0.5 μm, is used.

The polymerizable silicones produced by the method according to the invention have a high purity of at least 98.5% and a low content of by-products less than 0.4% each of the by-products monohydroxysilane, monoorganoxysilane and difunctional disiloxane.

Furthermore, the polymerizable silicones produced by the method according to the invention preferably have a salt content of less than 200 ppm, preferably of less than 150 ppm.

The polymerizable silicones according to the invention are used as raw materials and/or monomers for the production of electronic materials, for the production of contact lenses and optical components, as raw materials in compositions for functional and industrial coatings, for polymeric microstructures or cosmetics applications.

Example 1

3-methacryloxypropyltris(trimethylsiloxy)silane

In a three-neck flask, 75.4 g (0.47 mol) of hexamethyldisiloxane, 39.9 g (0.67 mol) of acetic acid, 8.7 g of sulfuric acid (conc.) (0.09 mol) and 0.5 g of a 10% solution of trifluoromethanesulfonic acid in acetic acid (0.0003 mol) are initially introduced and stirred at −15° C. to −5° C. At this temperature, 55.0 g (0.22 mol) of 3-methacryloxypropyltrimethoxysilane (Wacker GENIOSIL® GF 31) are metered in over the course of one hour. The mixture is then heated to room temperature and after-stirred for 2 h. After separating off the acidic lower phase from the organic layer, the organic phase is analyzed by means of GC: the following are found (besides the readily volatile constituents): product 49.6 area %; monoorganoxy impurity $CH_2=CH(CH_3)-COO-(CH_2)_3-Si(OSiMe_3)_2OMe$ (0.2 area %); monohydroxy impurity $(CH_2=CH(CH_3)-COO-(CH_2)_3-Si(OSiMe_3)_2OH$ (0.5 area %) and 0.5 area % of the difunctional disiloxane (dimers) $[CH_2=CH(CH_3)-COO-(CH_2)_3-Si(OSiMe_3)_2]O$.

To reduce the content of monohydroxysilane, at room temperature, 18.7 g (0.11 mol) of hexamethyldisilazane are added (1 h) and after-stirred for 1 h.

Following the reaction and neutralization with HMN and removal by filtration of the formed salt, the following constituents are identified in the crude product in the GC besides readily volatile constituents: product (45.5 area %); monoorganoxy impurity $CH_2=CH(CH_3)-COO-(CH_2)_3-Si(OSiMe_3)_2OMe$ (0.2 area %); monohydroxy impurity $CH_2=CH(CH_3)-COO-(CH_2)_3-Si(OSiMe_3)_2OH$ (0.0 area %) and 0.3 area % of the difunctional disiloxane (dimers) $[CH_2=CH(CH_3)-COO-(CH_2)_3-Si(OSiMe_3)_2]O$.

After distilling off the low-boiling components, the crude product has the following purities: product (97.8 area %); monoorganoxy impurity $CH_2=CH(CH_3)-COO-$ $(CH_2)_3$—$Si(OSiMe_3)_2OMe$ (0.2 area %); monohydroxy impurity $CH_2$=$CH(CH_3)$—COO—$(CH_2)_3$—$Si(OSiMe_3)_2$OH (0.0 area %) and 0.6 area % of the difunctional disiloxane (dimers) [$CH_2$=$CH(CH_3)$—COO—$(CH_2)_3$—$Si(OSiMe_3)_2$]O.

Following distillation and fine filtration (filter candle), the product 3-methacryloxypropyltris(tri-methylsiloxy)silane is obtained in 83% yield, the following GC contents being obtained: product (99.5 area %); monoorganoxy impurity $CH_2$=$CH(CH_3)$—COO—$(CH_2)_3$—$Si(OSiMe_3)_2OMe$ (0.2 area %); monohydroxy impurity $CH_2$=$CH(CH_3)$—COO—$(CH_2)_3$—$Si(OSiMe_3)_2$OH (0.0 area %) and 0.0 area % of the difunctional disiloxane (dimers) [$CH_2$=$CH(CH_3)$—COO—$(CH_2)_3$—$Si(OSiMe_3)_2$]O.

The results are summarized in the table below.

Comparative Experiment 1

The reaction was carried out analogously to example 1 according to the invention, except that (analogously to JP 11-217389 Dow Corning Toray) a significantly smaller amount of hexamethyldisilazane (0.12 g; 0.75 mmol) was added.

Following the reaction and separating off of the acidic lower layer, the organic phase is analyzed by means of GC: the following are found (besides the readily volatile constituents): product (49.1 area %); monoorganoxy impurity $CH_2$=$CH(CH_3)$—COO—$(CH_2)_3$—$Si(OSiMe_3)_2OMe$ (0.2 area %); monohydroxy impurity $CH_2$=$CH(CH_3)$—COO—$(CH_2)_3$—$Si(OSiMe_3)_2$OH (0.5 area %) and 0.5 area % of the difunctional disiloxane (dimers) [$CH_2$=$CH(CH_3)$—COO—$(CH_2)_3$—$Si(OSiMe_3)_2$]O.

Following the reaction and neutralization with HMN and removal by filtration of the formed salt, the following constituents are identified in the crude product by means of GC besides readily volatile constituents: product (51.6 area %); monoorganoxy impurity $CH_2$=$CH(CH_3)$—COO—$(CH_2)_3$—$Si(OSiMe_3)_2OMe$ (0.2 area %); monohydroxy impurity $CH_2$=$CH(CH_3)$—COO—$(CH_2)_3$—$Si(OSiMe_3)_2$OH (0.5 area %) and 0.3 area % of the difunctional disiloxane (dimers) [$CH_2$=$CH(CH_3)$—COO—$(CH_2)_3$—$Si(OSiMe_3)_2$]O.

After distilling off the low-boiling components, the crude product has the following purities: product (96.6 area %); monoorganoxy impurity $CH_2$=$CH(CH_3)$—COO—$(CH_2)_3$—$Si(OSiMe_3)_2OMe$ (0.2 area %); monohydroxy impurity $CH_2$=$CH(CH_3)$—COO—$(CH_2)_3$—$Si(OSiMe_3)_2$OH (0.8 area %) and 0.8 area % of the difunctional disiloxane (dimers) [$CH_2$=$CH(CH_3)$—COO—$(CH_2)_3$—$Si(OSiMe_3)_2$]O.

Following distillation and fine filtration (filter candle) the product 3-methacryloxypropyltris(tri-methylsiloxy)silane is obtained in 72% yield, the following GC contents being determined: product (98.4 area %); monoorganoxy impurity $CH_2$=$CH(CH_3)$—COO—$(CH_2)_3$—$Si(OSiMe_3)_2OMe$ (0.2 area %); monohydroxy impurity $CH_2$=$CH(CH_3)$—COO—$(CH_2)_3$—$Si(OSiMe_3)_2$OH (1.0 area %) and 0.0 area % of the difunctional disiloxane (dimers) [$CH_2$=$CH(CH_3)$—COO—$(CH_2)_3$—$Si(OSiMe_3)_2$]O.

The results are summarized in the table below.

Comparative Experiment 2 According to JP 2000-186095

The reaction was carried out analogously to example 1 according to the invention except that no hexamethyl-disilazane was added, but instead, after the reaction, an aging of the material (18 h at 25° C.) was carried out and then the reaction mixture was neutralized by washing five times with water (analogously to JP 2000-186095, Chisso).

After washing and phase separation, the reaction mixture was distilled analogously to example 1 according to the invention.

After the primary reaction, the organic phase is analyzed by means of GC: the following are found (besides the readily volatile constituents): product (48.6 area %); monoorganoxy impurity $CH_2$=$CH(CH_3)$—COO—$(CH_2)_3$—$Si(OSiMe_3)_2OMe$ (0.3 area %); monohydroxy impurity $CH_2$=$CH(CH_3)$—COO—$(CH_2)_3$—$Si(OSiMe_3)_2$OH (0.5 area %) and 0.5 area % of the difunctional disiloxane (dimers) [$CH_2$=$CH(CH_3)$—COO—$(CH_2)_3$—$Si(OSiMe_3)_2$]O.

The GC analysis after the aging process shows: product (49.2 area %); monoorganoxy impurity $CH_2$=$CH(CH_3)$—COO—$(CH_2)_3$—$Si(OSiMe_3)_2OMe$ (0.2 area %); monohydroxy impurity $CH_2$=$CH(CH_3)$—COO—$(CH_2)_3$—$Si(OSiMe_3)_2$OH (0.5 area %) and 0.6 area % of the difunctional disiloxane (dimers) [$CH_2$=$CH(CH_3)$—COO—$(CH_2)_3$—$Si(OSiMe_3)_2$]O.

Following the neutralization by washing several times with water (including phase separation), the reaction mixture exhibits the following composition: product (68.0 area %); monoorganoxy impurity $CH_2$=$CH(CH_3)$—COO—$(CH_2)_3$—$Si(OSiMe_3)_2OMe$ (0.2 area %); monohydroxy impurity $CH_2$=$CH(CH_3)$—COO—$(CH_2)_3$—$Si(OSiMe_3)_2$OH (0.5 area %) and 0.9 area % of the difunctional disiloxane (dimers) [$CH_2$=$CH(CH_3)$—COO—$(CH_2)_3$—$Si(OSiMe_3)_2$]O.

After distilling off the low-boiling components, the crude product has the following purities: product (97.3 area %); monoorganoxy impurity $CH_2$=$CH(CH_3)$—COO—$(CH_2)_3$—$Si(OSiMe_3)_2OMe$ (0.2 area %); monohydroxy impurity $CH_2$=$CH(CH_3)$—COO—$(CH_2)_3$—$Si(OSiMe_3)_2$OH (0.8 area %) and 1.2 area % of the difunctional disiloxane (dimers) [$CH_2$=$CH(CH_3)$—COO—$(CH_2)_3$—$Si(OSiMe_3)_2$]O.

Following distillation and fine filtration (filter candle, 0.2 μm) the product 3-methacryloxypropyltris (trimethylsiloxy)silane is obtained in 75% yield, the following GC contents being ascertained: product (98.2 area %); monoorganoxy impurity $CH_2$=$CH(CH_3)$—COO—$(CH_2)_3$—$Si(OsiMe_3)_2OMe$ (0.3 area %); monohydroxy impurity $CH_2$=$CH(CH_3)$—COO—$(CH_2)_3$—$Si(OsiMe_3)_2$OH (0.9 area %) and 0.0 area % of the difunctional disiloxane (dimers) [$CH_2$=$CH(CH_3)$—COO—$(CH_2)_3$—$Si(OSiMe_3)_2$]O.

The results are summarized in the table.

Comparative Experiment 3 According to JP 11-217389

The reaction was carried out analogously to example 1 according to the invention except that it was carried out at a temperature of 45° C. instead of a temperature at −15° C. to −5° C. After the reaction has taken place and the acidic lower phase has been separated off from the organic layer, the organic phase is analyzed by means of GC: the following are found (besides the readily volatile constituents): product 43.5 area %; monoorganoxy impurity $CH_2$=$CH(CH_3)$—COO—$(CH_2)_3$—$Si(OSiMe_3)_2OMe$ (0.5 area %); monohydroxy impurity $CH_2$=$CH(CH_3)$—COO—$(CH_2)_3$—$Si(OSiMe_3)_2$OH (0.9 area %) and 6.7 area % of the difunctional disiloxane (dimers) [$CH_2$=$CH(CH_3)$—COO—$(CH_2)_3$—$Si(OSiMe_3)_2$]O.

To reduce the content of monohydroxysilane, at room temperature, 18.7 g (0.11 mol) of hexamethyldisilazane are added (1 h) and after-stirred for 1 h.

Following the reaction and neutralization with HMN and after the formed salt has been filtered off, the following constituents are identified in the crude product in the GC besides readily volatile constituents: product (41.9 area %); monoorganoxy impurity $CH_2\!=\!CH(CH_3)\!-\!COO\!-\!(CH_2)_3\!-\!Si(OSiMe_3)_2OMe$ (0.5 area %); monohydroxy impurity $CH_2\!=\!CH(CH_3)\!-\!COO\!-\!(CH_2)_3\!-\!Si(OSiMe_3)_2OH$ (0.1 area %) and 6.9 area % of the difunctional disiloxane (dimers) $[CH_2\!=\!CH(CH_3)\!-\!COO\!-\!(CH_2)_3\!-\!Si(OSiMe_3)_2]O$.

After distilling off the low-boiling components, the crude product has the following purities: product (89.8 area %); monoorganoxy impurity $CH_2\!=\!CH(CH_3)\!-\!COO\!-\!(CH_2)_3\!-\!Si(OSiMe_3)_2OMe$ (0.8 area %); monohydroxy impurity $CH_2\!=\!CH(CH_3)\!-\!COO\!-\!(CH_2)_3\!-\!Si(OSiMe_3)_2OH$ (0.1 area %) and 7.1 area % of the difunctional disiloxane (dimers) $[CH_2\!=\!CH(CH_3)\!-\!COO\!-\!(CH_2)_3\!-\!Si(OSiMe_3)_2]O$.

After distillation and fine filtration (filter candle) the product 3-methacryloxypropyltris(trimethylsiloxy)silane is obtained in 71% yield, the following GC contents being ascertained: product (96.9 area %); monoorganoxy impurity $CH_2\!=\!CH(CH_3)\!-\!COO\!-\!(CH_2)_3\!-\!Si(OSiMe_3)_2OMe$ (0.7 area %); monohydroxy impurity $CH_2\!=\!CH(CH_3)\!-\!COO\!-\!(CH_2)_3\!-\!Si(OSiMe_3)_2OH$ (0.1 area %) and 0.7 area % of the difunctional disiloxane (dimers) $[CH_2\!=\!CH(CH_3)\!-\!COO\!-\!(CH_2)_3\!-\!Si(OSiMe_3)_2]O$.

The results are summarized in the table below.

TABLE

|  | Example 1 | Comparison 1 | Comparison 2 | Comparison 3 |
|---|---|---|---|---|
| After reaction at | −15° C. to −5° C. | −15° C. to −5° C. | −15° C. to −5° C. | 45° C. |
| Content of monoorganoxy | 0.2% | 0.2% | 0.3% | 0.5 |
| Content of monohydroxy | 0.5% | 0.5% | 0.5% | 0.9 |
| Content of disiloxane | 0.5% | 0.5% | 0.5% | 6.7 |
| Content of product | 49.6% | 49.1% | 48.6% | 43.5 |
| Aging | None | None | 18 h (25° C.) | None |
| Content of monoorganoxy |  |  | 0.2% |  |
| Content of monohydroxy |  |  | 0.5% |  |
| Content of disiloxane |  |  | 0.6% |  |
| Content of product |  |  | 49.2% |  |
| Removal of acidic phase | yes | yes | upon neutralization | HMN |
| Neutralization | HMN | HMN | H20 | HMN |
| Molar ratio [HMN/alkoxysilane] | 0.5 | 0.003 | — | 0.5 |
| Content of monoorganoxy | 0.2% | 0.2% | 0.2% | 0.5 |
| Content of monohydroxy | 0.0% | 0.5% | 0.5% | 0.1 |
| Content of disiloxane | 0.3% | 0.3% | 0.9% | 6.9 |
| Content of product | 45.5% | 51.6% | 68.0% | 41.9 |
| Product after distilling off the low boiling component |  |  |  |  |
| Content of monoorganoxy | 0.2% | 0.2% | 0.2% | 0.8 |
| Content of monohydroxy | 0.0% | 0.8% | 0.8% | 0.1 |
| Content of disiloxane | 0.6% | 0.8% | 1.2% | 7.1 |
| Content of product | 97.8% | 96.6% | 97.3% | 89.8 |

TABLE-continued

|  | Example 1 | Comparison 1 | Comparison 2 | Comparison 3 |
|---|---|---|---|---|
| End product after distillation and filtration |  |  |  |  |
| Content of monoorganoxy | 0.2% | 0.2% | 0.3% | 0.7 |
| Content of monohydroxy | 0.0% | 1.0% | 0.9% | 0.1 |
| Content of disiloxane | 0.0% | 0.0% | 0.0% | 0.7 |
| Content of product | 99.5% | 98.4% | 98.2% | 96.9 |
| Yield | 83% | 72% | 75% | 71 |

Example 2

1-methacryloxymethyltris(trimethylsiloxy)silane

The reaction was carried out analogously to example 1 according to the invention except that instead of 55.0 g (0.22 mol) of 3-methacryloxypropyltrimethoxysilane (Wacker GENIOSIL® GF 31), 48.8 g (0.22 mol) of 1-methacryloxymethyltrimethoxysilane (Wacker GENIOSIL® XL 33) were used. The desired product is ultimately obtained in a yield of 78%. (GC purity: 99.2% of 1-methacryloxymethyltris(trimethylsiloxy)silane (0.2 area % of monoorganoxysilane). Monohydroxy impurity and difunctional disiloxane can no longer be detected.

Example 3

1-methacryloxymethylbis(trimethyl-siloxy)methylsilane

The procedure is analogous to example 1. Instead of 55.0 g (0.22 mol) of 3-methacryloxypropyltrimethoxysilane (Wacker GENIOSIL® GF 31), in the present example 44.9 g (0.22 mol) of 1-methacryloxymethyldimethoxymethylsilane (Wacker GENIOSIL® XL 32) and only 56.7 g (0.35 mol) of hexamethyldisiloxane are used. The desired product is ultimately obtained in a yield of 81%. GC purity: 99.4% of 1-methacryloxymethylbis(trimethylsiloxy)methylsilane (0.1 area % of monoorganoxysilane). Monohydroxy impurity and difunctional disiloxane can no longer be detected.

Example 4

Vinyltris(trimethylsiloxy)silane

The procedure is analogous to example 1. Instead of 55.0 g (0.22 mol) of 3-methacryloxypropyltrimethoxysilane (Wacker GENIOSIL® GF 31), in the present example 32.6 g (0.22 mol) of vinyltrimethoxysilane are used. The desired product is ultimately obtained in a yield of 83%. GC purity: 99.3% of vinyltris(trimethylsiloxy)silane (0.2 area % of monoorganoxysilane). Monohydroxy impurity and difunctional disiloxane can no longer be detected.

The invention claimed is:
1. A process for the production of polymerizable silicones of the formula

$$P\!-\!Y\!-\!Sp\!-\!Si(R^2)_n(OSiR^1{}_3)_{(3-n)} \qquad (I),$$

comprising the following steps:
(a) admixing disiloxane (1) of the formula

  (II)

with acetic acid (2) and sulfuric acid (3) and optionally acidic catalyst (4),
(b) at a temperature of from −20° to 0° C., metering in a substituted alkoxysilane (5) of the formula P—Y-Sp-Si($R^2$)$_n$(O$R^3$)$_{(3-n)}$  (III), (c) following a phase separation, separating off an acid phase from a product phase,
(d) adding 0.02-1.0 mol of hexamethyldisilazane (6), based on 1 mol of alkoxysilane (5) to the product phase,
(e) after filtering off a resulting salt from the product phase, removing readily volatile constituents and distilling to recover a polymerizable silicone product, and
(f) optionally filtering the product,
where
$R^1$ are each identical or different and are hydrogen or an optionally substituted monovalent hydrocarbon radical having 1 to 18 carbon atoms,
$R^2$ are each identical or different and are hydrogen or an optionally substituted monovalent hydrocarbon radical having 1 to 18 carbon atoms,
$R^3$ are each identical or different and are alkyl radicals having 1 to 18 carbon atoms optionally substituted with alkoxy groups,
Sp is a single bond or a divalent hydrocarbon radical having 1 to 8 carbon atoms,
Y is a single bond or —O—,
P is an acryloxy, methacryloxy, vinyl or allyl radical, and
n is 0, 1 or 2.

2. The process of claim 1, wherein the sulfuric acid is concentrated sulfuric acid.

3. The process of claim 1 where n is 0.

4. The process of claim 2 where n is 0.

5. The process of claim 1, wherein the molar ratio of disiloxane (1) and alkoxysilane (5) is 0.5 to 1.0 mol of disiloxane (1) per mole of alkoxy group of the alkoxysilane (5).

6. The process of claim 1, wherein the molar ratio of disiloxane (1) and alkoxysilane (5) is 0.6 to 0.8 mol of disiloxane (1) per mole of alkoxy group of the alkoxysilane (5).

7. The process of claim 2, wherein the molar ratio of disiloxane (1) and alkoxysilane (5) is 0.6 to 0.8 mol of disiloxane (1) per mole of alkoxy group of the alkoxysilane (5).

8. The process of claim 1, wherein step (b), the alkoxysilane (5) is metered in over the course of 1 h-3 h and is then post-reacted at 10° C.-45° C. for 1 h-4 h.

9. The process of claim 5, wherein step (b), the alkoxysilane (5) is metered in over the course of 1 h-3 h and is then post-reacted at 10° C.-45° C. for 1 h-4 h.

10. The process of claim 1, wherein the alkoxysilane (5) is 3-methacryloxypropyltrimethoxysilane.

11. The process of claim 5, wherein the alkoxysilane (5) is 3-methacryloxypropyltrimethoxysilane.

12. The process of claim 8, wherein the alkoxysilane (5) is 3-methacryloxypropyltrimethoxysilane.

13. The process of claim 1, wherein the disiloxane (1) is hexamethyldisiloxane.

14. The process of claim 1, wherein the process further comprises adding a stabilizer before or after the distillation.

15. The process of claim 1, wherein a stabilizer is added prior to distillation.

16. The process of claim 1, wherein at least one process step is carried out in the presence of oxygen.

* * * * *